US011998286B2

(12) United States Patent
Gaudreau (10) Patent No.: US 11,998,286 B2
(45) Date of Patent: Jun. 4, 2024

(54) QUICK CONNECT SYSTEM FOR SURGICAL NAVIGATION TOOLS

(71) Applicant: ORTHOSOFT ULC, Montreal (CA)

(72) Inventor: Jeremie Gaudreau, Ottawa (CA)

(73) Assignee: ORTHOSOFT ULC, Montreal (CA)

( * ) Notice: Subject to any disclaimer, the term of this patent is extended or adjusted under 35 U.S.C. 154(b) by 67 days.

(21) Appl. No.: 17/206,435

(22) Filed: Mar. 19, 2021

(65) Prior Publication Data

US 2021/0290312 A1 Sep. 23, 2021

Related U.S. Application Data

(60) Provisional application No. 62/991,728, filed on Mar. 19, 2020.

(51) Int. Cl.
*A61B 34/20* (2016.01)
*A61B 34/30* (2016.01)

(52) U.S. Cl.
CPC .............. *A61B 34/20* (2016.02); *A61B 34/30* (2016.02); *A61B 2034/2055* (2016.02); *A61B 2034/2068* (2016.02); *A61B 2560/0223* (2013.01)

(58) Field of Classification Search
CPC . A61B 34/20; A61B 34/30; A61B 2034/2055; A61B 2034/2068
See application file for complete search history.

(56) References Cited

U.S. PATENT DOCUMENTS

| 2012/0150155 | A1* | 6/2012 | Kappel | A61B 17/2909 606/1 |
| 2016/0235418 | A1* | 8/2016 | Mimran | A61B 17/1671 |
| 2018/0228520 | A1* | 8/2018 | Bobbitt | A61B 17/7002 |
| 2019/0357986 | A1* | 11/2019 | Morgan | A61B 34/20 |
| 2021/0106318 | A1* | 4/2021 | Melilli | A61B 17/00 |

FOREIGN PATENT DOCUMENTS

| CN | 108366840 | * | 8/2018 | ............. A61B 34/70 |
| WO | WO-2019018342 A1 | * | 1/2019 | ......... A61B 17/3403 |

* cited by examiner

*Primary Examiner* — Rochelle D Turchen
(74) *Attorney, Agent, or Firm* — NORTON ROSE FULBRIGHT CANADA LLP (57) ABSTRACT

A surgical tool assembly may include a first component, a second component, a tracker device connected at least to the first component. A quick connect system for releasably connecting the first component to the second component, the quick connect system including a male and female engagement, a latch mechanism for latching the first component to the second component. Complementary features are on the first component and on the second component to ensure a planned positional alignment between the first component and the second component upon latching of the male and female engagement, for tracking of the second component with the tracker device.

18 Claims, 9 Drawing Sheets

QUICK CONNECT SYSTEM FOR SURGICAL NAVIGATION TOOLS

CROSS-REFERENCE TO RELATED APPLICATION

The present application claims the priority of U.S. Patent Application No. 62/991,728, filed on Mar. 19, 2020, and incorporated herein by reference.

TECHNICAL FIELD

The application relates to computer-assisted surgery, in which surgical tools are tracked, and more particularly to a quick connect system used in such surgical tools.

BACKGROUND

Tracking of surgical instruments or tools is an integral part of computer-assisted surgery (hereinafter CAS). The tools are tracked for position and/or orientation in such a way that information pertaining to bodily parts is obtained. The information is then used in various interventions with respect to the body, such as bone alterations, implant positioning, incisions and the like.

For example, optical tracking systems are commonly used in the operating room, notably because active transmitters on the tools are not required on the tools, and therefore represent fewer issues pertaining to sterilization. The CAS system associated with such passive tracking has an optical sensor apparatus provided to visually detect optical elements on the tools. The optical elements are passive, whereby no power source is associated therewith. Other tracking technologies may involve inertial sensors, for example.

One issue with tracking systems stems from detachable trackers that must be attached to surgical tools. This may be done to simplify the tools, e.g., so as to have a tracker device per tool, to lessen the cost of tools, to limit the inventory of tracker devices, etc. However, the connection between tools and tracker devices must be solid and stable, as any play may have an impact on the precision of the tracking.

SUMMARY

In one aspect, there is provided a surgical tool assembly comprising: a first component; a second component; a tracker device connected at least to the first component; and a quick connect system for releasably connecting the first component to the second component, the quick connect system including a male and female engagement, a latch mechanism for latching the first component to the second component, and complementary features on the first component and on the second component to ensure a planned positional alignment between the first component and the second component upon latching of the male and female engagement, for tracking of the second component with the tracker device.

In another aspect, there is provided a system for tracking a surgical tool assembly in computer-assisted surgery, comprising: a processing unit, featuring one or more processors; and a non-transitory computer-readable memory communicatively coupled to the processing unit and comprising computer-readable program instructions executable by the processing unit to: track a first component in space during computer-assisted surgery using a tracker device on the first component; receive a notification that a second component is connected to the first component; automatically calibrate an assembly of the first component and the second component using a planned positional alignment between the first component and the second component; and track the second component assembled to the first component in space during computer-assisted surgery using the tracker device on the first component.

DESCRIPTION OF THE DRAWINGS

Reference is now made to the accompanying figures in which.

DETAILED DESCRIPTION

Figure 1:
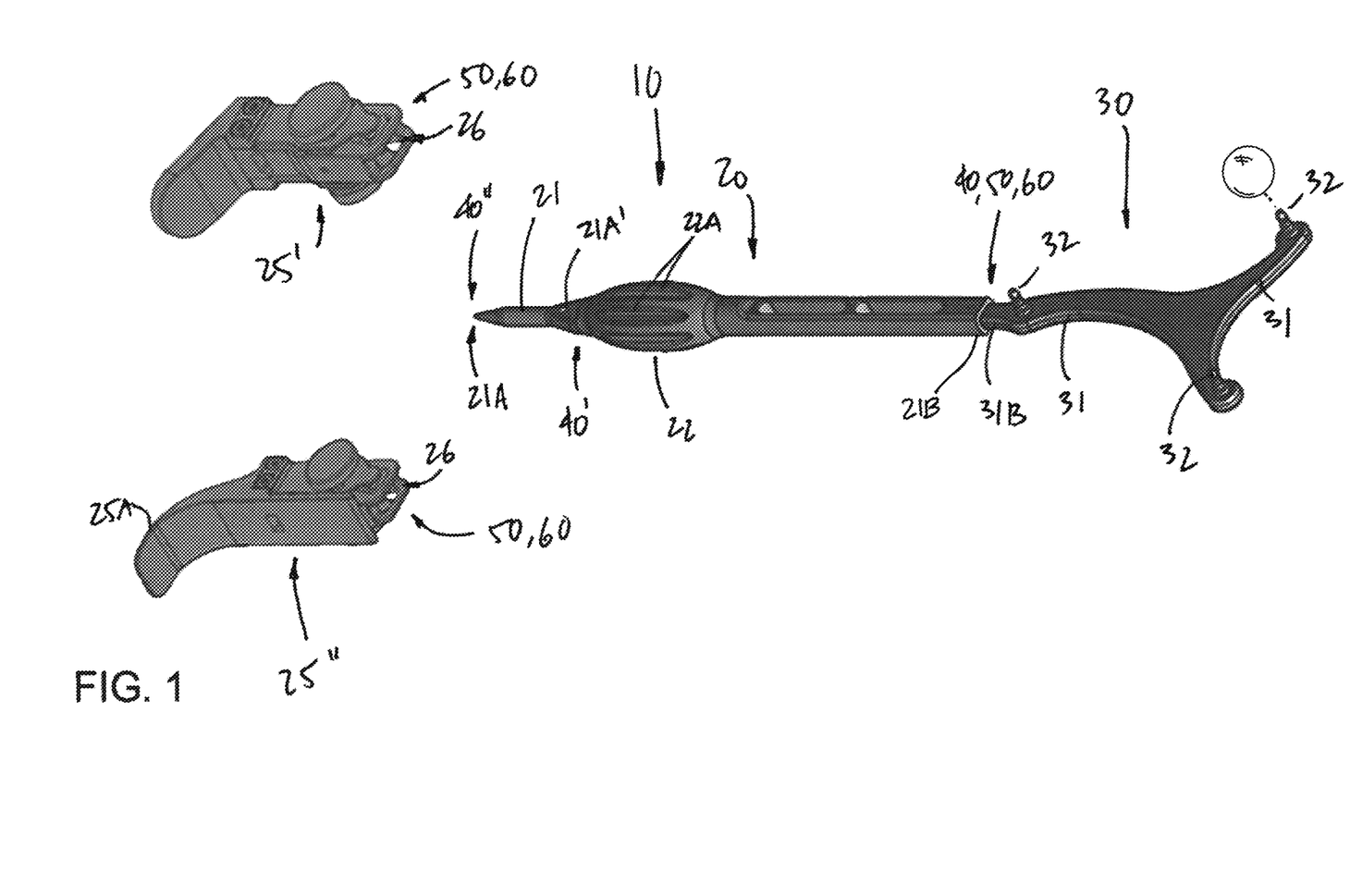
FIG. 1 is a perspective view of a surgical navigation tool assembly using a quick connect system in accordance with the present disclosure.

Referring to the drawings, and more particularly to FIG. 1, a surgical navigation tool assembly in accordance with the present disclosure is generally shown at 10. The surgical navigation tool assembly 10 is shown as including a registration pointer 20 used in an optical tracking context, and may also include a surface digitizer device 25, two of which are shown, with different bone interface surface geometries 25A. The surface digitizer devices are concurrently referred to as 25, but one of the surface digitizer devices 25 is labelled as 25' and the other is labelled 25" in FIG. 1. The surface digitizer device 25' is for instance used to validate or register a planar surface, such as a cut plane. The surface digitizer device 25" may be used to access non visible surfaces, such as bone surfaces under soft tissue, as an example. Other types of surface geometries 25A may be used. The present disclosure pertains to a quick connect system that may be used between a surgical tool and a tracker device, or between the surgical tool 20 and another surgical tool such as the surface digitizer devices 25, which may be known as extension, adaptors, etc. Hence the illustrated surgical navigation tool assembly 10 is an example among others. Just to name a few, surgical tools used as part of the surgical navigation tool assembly 10 may be a reamer, an awl, a saw, a drill, a cut guide, an impactor, a robot arm, base, etc. The tracker device may be optically recognized patterns, inertial sensors, active devices, among possibilities. The expression "quick connect" refers to a connection with interlocking components that are interlocked by a pushing action, for example, with biasing forces possibly involved to complete the interlocking action. Other expressions that could be used are snap fitting, interlocking, etc.

Now, for simplicity, the following description focuses on the registration pointer 20 with an optically-tracked device, with the surface digitizer devices 25, even though it may apply to different technologies, such as robotic systems, depth camera tracking, inertial sensors, etc. The surgical navigation tool assembly 10 has a surgical tool 20 in the exemplary form of a registration pointer, with a tracker device 30 thereon, with the registration pointer 20 being connected to the tracker device 30 by a quick connect system 40, 50 or 60 in accordance with the present disclosure, as a possibility. The quick connect system may be located at another end of the tool 20, as shown by 40', or may be between the tool 20 and the surface digitizer devices 25, as shown as 40". Again, the tool 20 may be any other type of surgical tool than the one shown. If the tool 20 is a registration pointer, it has a stem 21 (a.k.a., a shaft) having a working end 21A, i.e., the proximal end, and a distal end 21B. The working end 21A may be in the form of a tip, that may have a pointy shape, a rounded shape, hemispherical shape, etc. As the working end 21A comes into contact with soft tissue, for example in the context of registering some surface points, the position of the working end 21A is tracked and must be done so with precision and accuracy. A socket or sockets may be provided at 21A', for connection of the tool 20 to the surface digitizer devices 25 with the quick connect system 40, 50, or 60, as detailed below.

The distal end 21B may define a receptacle for the releasable connection of the tracker device 30 to the tool 20, using the quick connect system 40, 50 or 60. In such an arrangement, the receptacle may form a female connector. Various shapes and configurations of the receptacle at the distal end 21B are described below with reference to the quick connect system 40, 50, or 60. As mentioned above, it is also contemplated to have the quick connect system 40, 50 or 60 located at or near the working end 21A, also as shown in FIG. 1, by way of 40', or between the working end 21A and the surface digitizer device 25. In another embodiment, there are the quick connect system 40, 50 or 60, the quick connect system 40' and the quick connect system 40" for the surgical navigation tool assembly 10, for example to change the tip shape of the tool 20, the overall length of the tool 20 and/or type of body of the tool 20 or assembled to any of the surface digitizer devices 25 to the tool 20 to navigate the surface digitizer devices 25 with the tracker device 30. The tool 20 is shown having a particular configuration including a handle portion 22. The handle portion 22 may be closer to the distal end 21B, for example, or may have different shapes, etc. As another possibility, the change in the tip shape via the quick connect system 40' could for example give a different use to the tool 20, such as converting the tool 20 from a registration pointer to an impactor, as a possibility among others.

The handle portion 22 may generally outline an oval, as shown in FIG. 1, as a possibility among others. A plurality of gripping concavities 22A may be provided on a peripheral surface of the handle portion 22. The concavities 22A will facilitate the handling of the registration pointer, as fingertips of a pointer operator can be nested therein. The registration pointer 20 as a whole may be made of a sterilizable material, providing appropriate friction for ease of manipulation.

Still referring to FIG. 1, components of the tracker device 30 are illustrated. The tracker device 30 has a body having three or more prongs 31, with each prong 31 having a snap-fit pin 32. The snap-fit pins 32 are adapted to receive detectable devices thereon as shown, in snap-fitting engagement, such as retro-reflective spheres, one of which is illustrated. The three prongs 31 are in a predetermined pattern, so as to be recognized by a CAS system for tracking for position and orientation of the surgical navigation tool assembly 10, as will be explained in detail hereinafter. The predetermined pattern has the pins 32 arranged in a scalene triangle, for example. Other optical arrangements are for instance described in U.S. Pat. No. 8,386,022, incorporated herein by reference. Other tracking technologies may also be used, i.e., not only optical.

One of the prongs 31 of the tracker device 30 may have an extension 31B that may serve as male connector to be received in the receptacle at the distal end 21B of the tool 20. The reverse arrangement may be considered as well, such as with a female connector at the extension 31B. The extension 31B may be part of the quick connect system 40, as described below.

Figure 2:
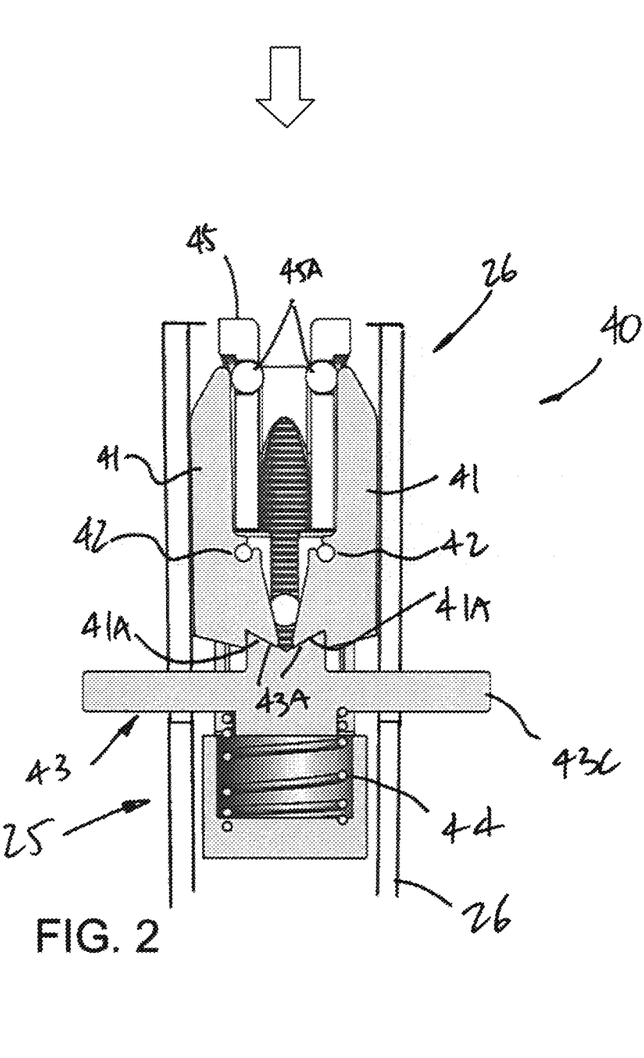
FIG. 2 is a longitudinal cross-section view of an embodiment of a quick connect system used in the surgical navigation tool assembly of FIG. 1.

Referring now to FIG. 2, one embodiment of the quick connect system 40, that shown at location 40" in FIG. 1, is shown in greater detail. The quick connect system 40 may for instance be located in a receptacle 26 of the surface digitizer devices 25 to receive therein the working end 21A of the tool 20. The quick connect system 40 may include one or more arms 41. A pair of arms 41 are shown as an example, which pair is shown in a symmetrical arrangement. The arms 41 may each have an elongated body with a depression 41A at a proximal end thereof. The arms 41 are pivotally inside the receptacle 26 in a fixed position, whereby the arms 41 are constrained to one rotational degree of freedom (DOF) in the receptacle 26.

A latch mechanism featuring a latch 43 may also be in the receptacle 26 at the distal end 21B. The latch 43 may have a pair of fingers 43A or like projections that project toward the arms 41. The fingers 43A may have a shape that is complementary to that of the depressions 41A for complementary engagement of fingers 43A in the depressions 41A. In an embodiment, when the complementary engagement is reached, as in FIG. 2 and FIG. 3C, the arms 41 and latch 43 are latched to one another, and an external force is required to release the latch 43. For example, the latch 43 may have wing(s) 43C that may project outside of the receptacle of the distal end 21B, for the latch 43 to be moved against the action of biasing device 44, to release the engagement. The biasing device 44, as shown as a coil spring as an example among others, may bias the latch 43 in a distal direction (upward in the page of FIGS. 2 and 3A-3C), to cause the latching action.

A sleeve 45 or like support or guide may be located between the arms 41. The sleeve 45 may for example hold balls 45A, or like surface features (e.g., cones, frustocones, truncated sphere, spherical portion, etc). The balls 45A may be on either side of the sleeve 45 and held captive therein, though with the possibility of moving transversely relative to an axis of the sleeve 45. The balls 45A are precisely located along the sleeve 45 to be received in the sockets 21A' of the tool 20 (FIG. 1) when the working end 21A of the tool 20 is inserted in the sleeve 45. In doing so, the working end 21A of the tool 20 displaces the proximal ends of the arms 41 away from one another and lodges in the sleeve 45, typically with a snug or tight fit.

Figure 3A:
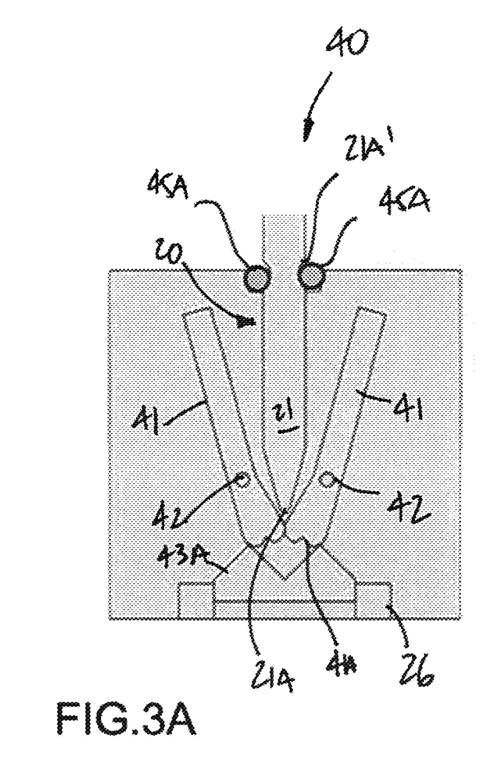
FIGS. 3A-3C are schematic views illustrating a sequence of engagement of a tracker device and surgical tool using a quick connect system as in FIG. 2.
Figure 3B:
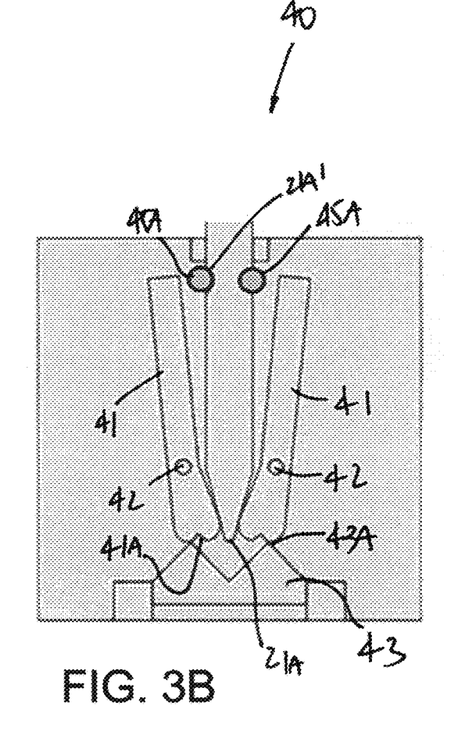
Figure 3C:
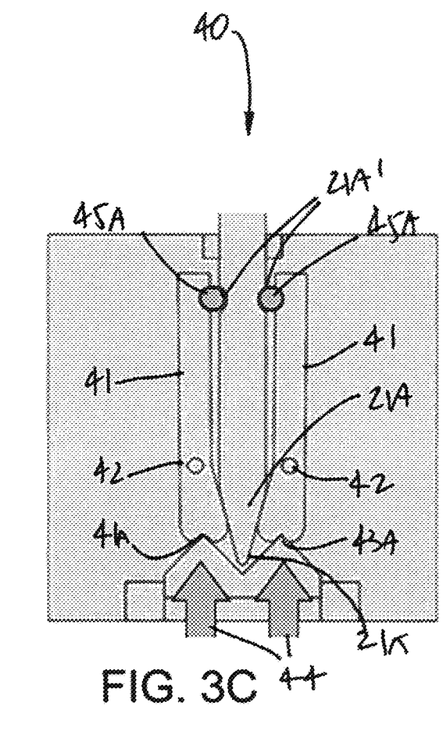

Accordingly, with reference to FIGS. 3A to 3C, a sequence of latching the tool 20 to the surface digitizer device 25, using the quick connect system 40, is detailed. The quick connect system 40 in FIGS. 3A and 3C differs from the one shown in FIG. 2 in various aspects, but the operation of the latching is generally the same.

Referring to FIG. 3A, as the tool 20 is received in the receptacle 26 of the surface digitizer device 25 and displaced in a proximal direction, along the longitudinal axis of the tool 20 for example, the working end 21A of the tool 20 comes into contact with proximal portions of the arms 41. This will result in a pivoting motion of the arms 41, as shown when comparing FIGS. 3A and 3B. The fingers 43A of the latch 43 may move along the surface of the arms 41, which may result in a movement of the latch 43 in a proximal direction (i.e., downwardly in FIGS. 3A-3C), against the action of the biasing device 44 (FIG. 2).

The various components are sized such that when the working end 21A is at a given depth in the receptacle 26, the fingers 43A latch into the depressions 41A. Simultaneously, the balls 45A are received in the sockets 21A'. FIG. 3A is schematic and therefore does not show that the balls 45A are not in the sockets 21A' as they should be in this figure. Due to the shape of the balls 45A and their mating engagement into the sockets 21A', the depth of penetration of the tip 21A in the receptacle 26 is known with precision, as it is correlated to the precise distance between the tip of the working end 21A and the sockets 21A'. Hence, the tool 20 and the surface digitizer device 25 are locked to one another. Using the geometry data of the tool 20 and of the surface digitizer device 25 (i.e., length, orientation), the position, and possibly the orientation, of the interface surface 25A may be calculated, using the position and orientation of the tracker device 30. The movements described above may occur automatically as a response to the manual insertion of the tool 20 in the surface digitizer device 25, or vice-versa. For this purpose, the quick connect system 40 is referred to as "quick connect" as per terminology used for similar snap-it, manually induced automatic connections. Other expressions could be used to qualify the system 40, such as connection system, snap-fit system, etc.

To release the tool 20 from the surface digitizer device 25, a user may displace the latch 43 from its engagement with the arms 41. For example, this is done by pulling the latch 43 in the proximal direction, for example, via the wing(s) 43. The tracker device 30 may be displaced in the distal direction, i.e., pulled away, to release the tool 20 from the surface digitizer device 25.

Therefore, the sockets 21A' and balls 45A are complementary features on the tool 20 and on the surface digitizer device 25 to ensure axial alignment between the tool 20 and the surface digitizer device 25, e.g., along the distal-proximal direction. As mentioned above, other complementary features may be used, such as conically tapered joints, as an example, that self-align when engaged into one another due to the complementary shapes. Examples are provided below of other self-alignment complementary features for the axial alignment, such as the conically tapered joints.

Referring now to FIGS. 4-9, another embodiment of the quick connect system is shown at 50, and may be used in the surgical navigation tool assembly 10 of FIG. 1, for connection of the tool 20 to a surface digitizer device 25. The quick connect system 50 is integrated into the receptacle 26 of the distal end of the surface digitizer devices 25. In other embodiments, the receptacle could be at the proximal end of the tracker device 30, with the quick connect system 50 integrated in the tracker device 30. The receptacle is shown at 51, and defines inner cavity 52, in which a male connector, such as the working end 21A of the tool 20, is received. The working end 21A may define the sockets 21A' for the latching of the tool 20 to the receptacle 41. In another embodiment, the receptacle is part of a rectangular-section tube, but other cross-sectional shapes are considered as well. A latch mechanism may include tongues 53 may be defined in opposite sides of the receptacle 51. Accordingly, the figures show tongues 53A and 53B, while the text refers to the tongues concurrently as 53. For the quick connect system 50, the letters A or B in the figures will be indicative of whether the components are related to tongue 53A or tongue 53B.

The tongues 53 may be described as leaf springs, for example, as they are connected to a body of the receptacle 51 at one end, the connection end, and have a cantilevered end away from the connection end. The cantilevered end may have a head portion, narrowing with a neck to its connection end, as shown as an exemplary shape among others. In an embodiment, the tongues 53 are an integral part of the receptacle 51, even monolithic as shown, and are defined by channels 54 contouring the tongues 53. The channels 54 may be laser cut channels, machined channels, etc. In an embodiment, the tongues 53 are coplanar with the walls of the receptacle 51 in which they are formed. However, other arrangements are considered. The material and dimensions of the tongues 53 are selected such that the tongues 53 exhibit elastic deformation in quick connect use as described below.

The tongues 53 may have slots 55 in the cantilevered end. The slots 55 may extend through the tongues 53. An arm 56 is secured into one of the slots 55, and passes through the slot 55 in the opposite tongue 53. Stated differently, the tongue 53A has an arm 56A received and fixed in one of its slots 55A. The arm 56A passes through the inner cavity 52, and through one of the slots 55B of the other tongue 53B, to extend out of the receptacle 51. A detent 57A is located at the end of the arm 56A, and is located outside of the receptacle 51. The detent 57A may be referred to as a button, a push button, etc. The interplay between the tongues 53A and 53B is particularly well observed in FIGS. 8 and 9. The same arrangement may be replicated for the other tongue 53B, as it may have slots 55B, arm 56B, and detent 57B. In an embodiment, there is only one slot 55 in each tongue 53, as the arm 56 may be connected to a surface of the tongue 53 instead of being received in a slot 55. Again, other arrangements are contemplated.

Figure 8:
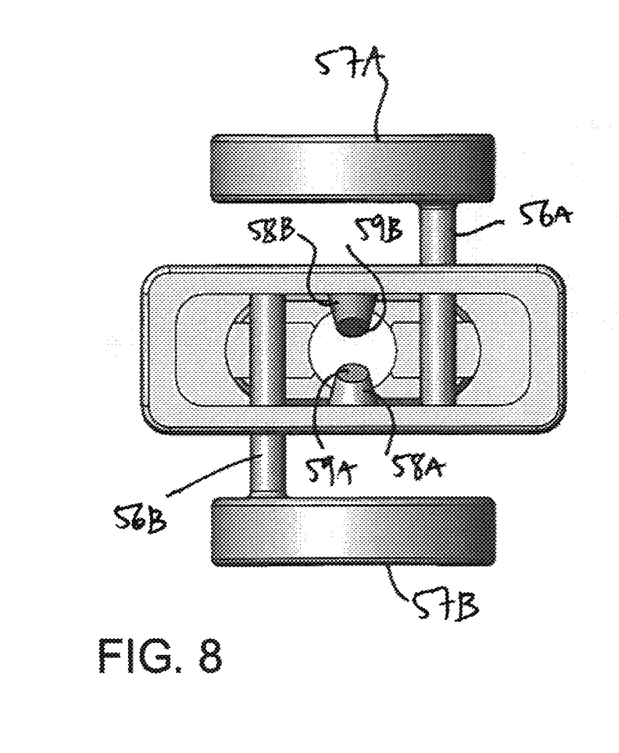
FIG. 8 is a top view of the quick connect system of FIG. 4.
Figure 9:
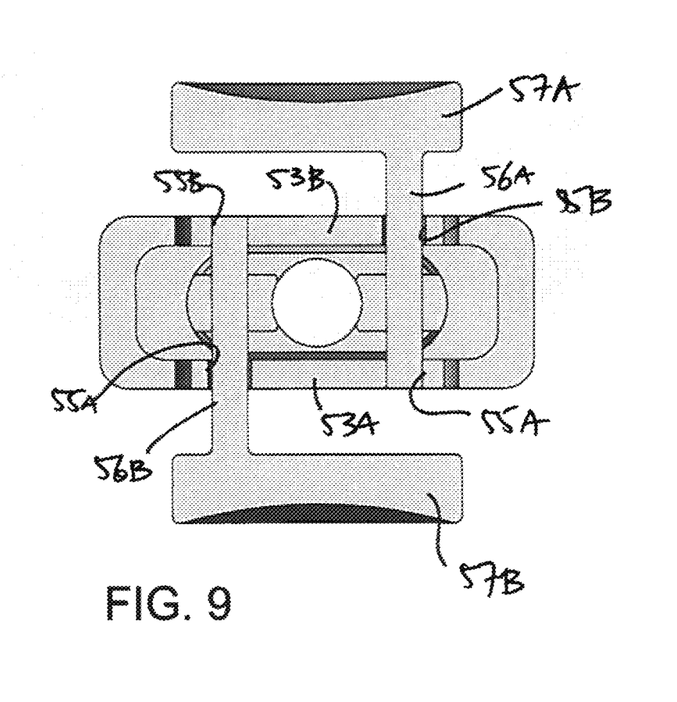
FIG. 9 is a cross section view of the quick connect system of FIG. 4.

The arms 56 may be parallel to one another, and when applying a pinching force on the detents 57, as shown in FIG. 9, the cantilevered ends of the tongues 53 may be spaced apart from one another by elastic deformation, with the possibility of returning to the shape of FIGS. 8 and 9 by the resilience of the tongues 53. The arms 56 may in an embodiment form guideways for the working end 21A of the tool 20, to remove play and ensure translational or sliding movement.

Latch bolts 58 may be formed on the tongues 53, and may be located inside the inner cavity 52. The latch bolts 58 may for instance face one another, and may be in the cantilevered end. In an embodiment, the latch bolts 58 have a frusto-conical shape, but other shapes are contemplated, including cylinders, spheres, etc. Moreover, an end surface 59 of the latch bolts 58 may be slanted, such that axes of the frustocones are not normal to the end surfaces 59.

Figures 4, 5:
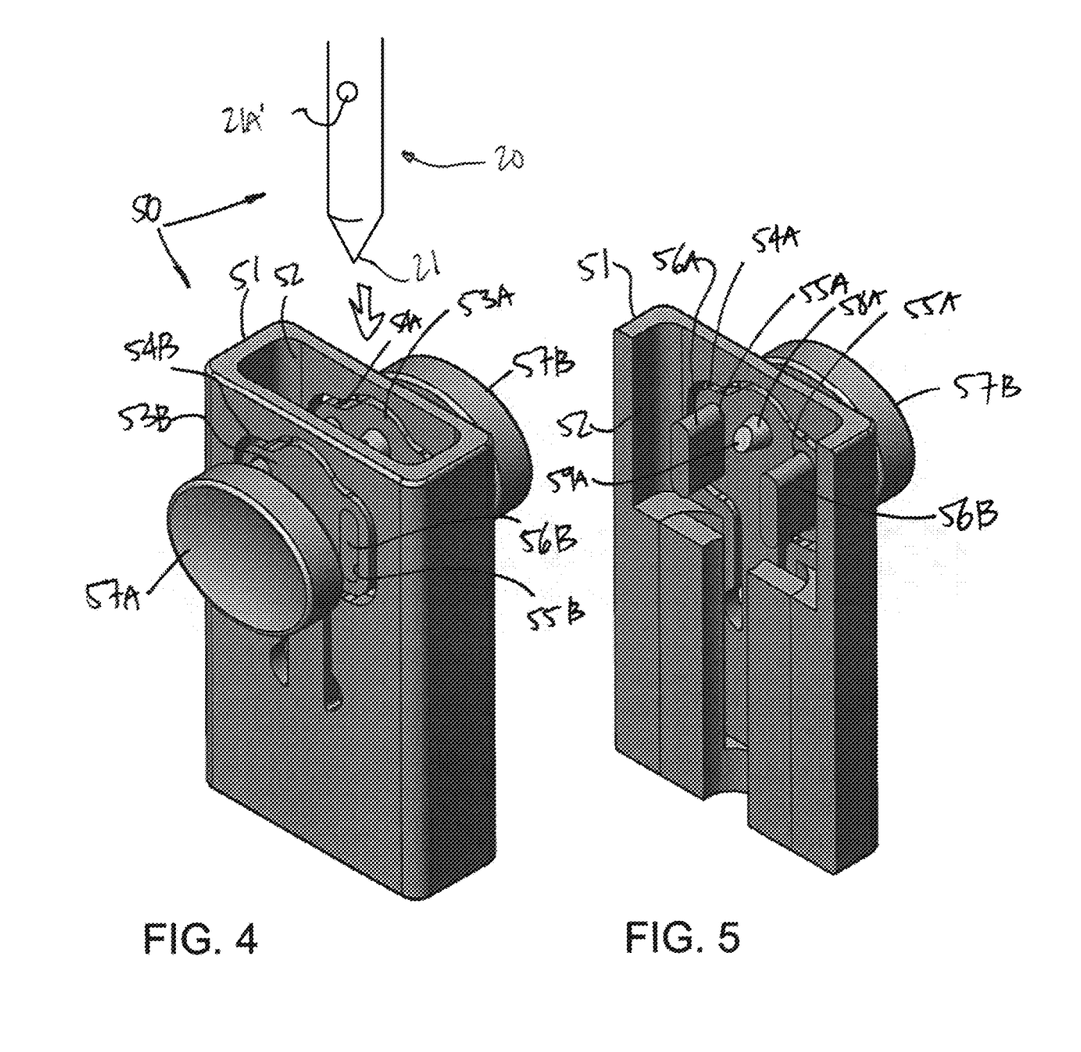
FIG. 4 is a perspective view of another embodiment of a quick connect system used in the surgical navigation tool assembly of FIG. 1.
FIG. 5 is a longitudinal section view of the quick connect system of FIG. 4.
Figure 6:
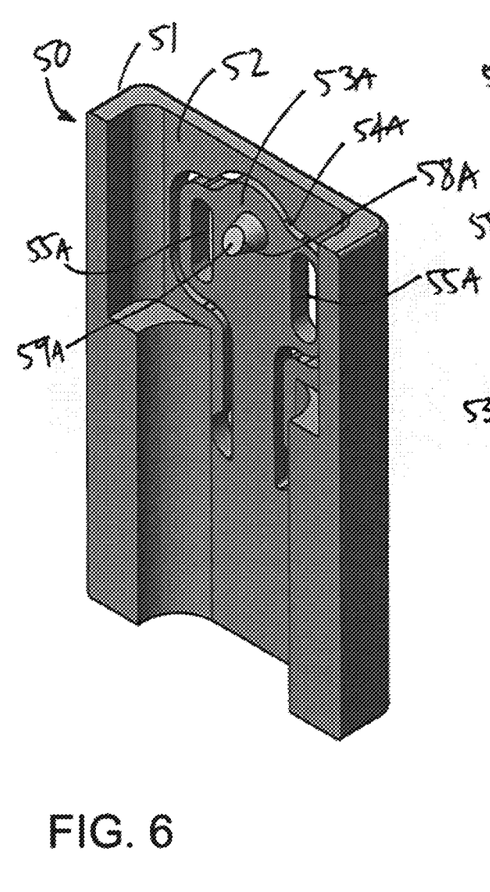
FIG. 6 is another longitudinal section view of the quick connect system of FIG. 4 showing only a tongue.
Figure 7:
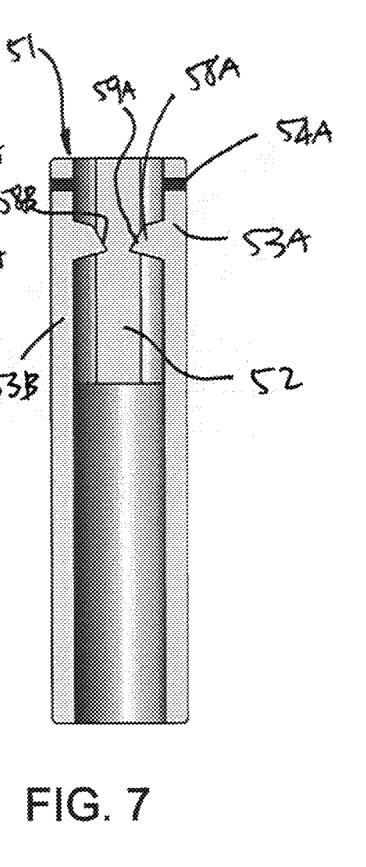
FIG. 7 is another longitudinal section view of the quick connect system of FIG. 4, showing only tongues.

Accordingly, with reference to FIGS. 4 to 9, a sequence of latching the tool 20 to the surface digitizer device 25, using the quick connect system 50, is detailed. In FIG. 4, the working end 21A is moved in a proximal direction toward the receptacle 51 to be received in the inner cavity 52, along the longitudinal axis of the tool 20 for example. In an embodiment, the working end 21A has a thickness corresponding to a width of the inner cavity 52 to avoid lateral play. The working end 21A of the tool 20 comes into contact with the latch bolts 58. Due to the frustoconical shape (or equivalent, such as hemispherical shape), the working end 21A slides along the latch bolts 58, and this may include sliding along the surfaces 59. This will result in a pivoting motion of the tongues 53. The latch bolts 58 then come into axial alignment with the sockets 21A' in the tool 20. The biasing force resulting from the deformation of the tongues 53 (e.g., elastic deformation), will cause a penetration of the latch bolts 58 into the sockets 21A', i.e., a latch. The sockets 21A' are shaped for complementary engagement with the latch bolts 58, and this may include for example a complementary frustoconical hole shape. The sockets 21A' may for instance be hemispherical in shape or have any other concave feature to act as a receptacle. The sockets 21A' and the latch bolts 58 may be conically tapered joints that self-align for the tool 20 and the surface digitizer device 25 to be in a predetermined axial alignment. There may hence result a positional alignment between the tool 20 and the surface digitizer device 25, that is as planned. Stated differently, once a first component and a second component, such as the tool 20 and the surface digitizer device 25, are coupled by the quick connect, the interrelation between the components is known as it was planned, and hence the coupling may be referred to as a planned positional alignment, planned positional coupling, planned positional connection.

The various components are sized such that when the working end 21A is at a given depth in the receptacle 51, the latch bolts 58 latch into the sockets 21A'. Due to the shape of the bolts 58 and their mating engagement into the sockets 21A', the depth of penetration of the working end 21A in the receptacle 51 is known with precision. Hence, the tool 20 and the surface digitizer device 25 are locked to one another by the quick connect system 50. Using the geometry data of the tool 20 and of the surface digitizer device 25 (i.e., length, orientation), the position, and possibly the orientation, of the interface surface 25A may be calculated, using the position and orientation of the tracker device 30. The movements described above may occur automatically as a response to the manual insertion of the tool 20 in the surface digitizer device 25, or vice-versa. For this purpose, the quick connect system 50 is also referred to as "quick connect" as per terminology used for similar snap-it, manually induced automatic connections. Other expressions could be used to qualify the system 50, such as connection system, snap-fit system, etc.

To release the tool 20 from the surface digitizer device 25, a user may press on the detents 57 to displace the latch bolts 58 from their inserted engagement into the sockets 21A'. The tool 20 may be displaced in the distal direction, i.e., pulled away, to release the surface digitizer device 25 from the tool 20.

Referring now to FIGS. 10-13, another embodiment of the quick connect system is shown at 60, and may be used in the surgical navigation tool assembly 10 of FIG. 1. Similarly to the quick connect system 50, the quick connect system 60 is integrated into the receptacle 26 of the surface digitizer device 25, but could be elsewhere, such as between the tool 20 and the tracker device 30. The receptacle is shown at 61, and defines inner cavity 62, in which a male connector, such as working end 21A, is received. The working end 21A may define the sockets 21A' for the latching of the working end 21A to the receptacle 41, though as in all embodiments the socket may be in the quick connect system with the tool featuring the balls or like penetrating component (e.g. latch bolt). In an embodiment, the receptacle is part of a rectangular-section tube, but other cross-sectional shapes are considered as well. The receptacle 61 may also include passages 61P and holes 61H.

The quick connect system 60 is similar in operation to the quick connect system 50, but tongues 63 are not made from a cutout in a wall of the receptacle 61, but are instead separate parts. The tongues 63 may be located in opposite sides of the receptacle 61, for instance as a U-shaped bracket as observed from FIG. 11. Accordingly, the figures show tongues 63A and 63B, while the text refers to the tongues concurrently as 63. For the quick connect system 60, the letters A or B in the figures will be indicative of whether the components are related to tongue 63A or tongue 63B.

Figure 11:
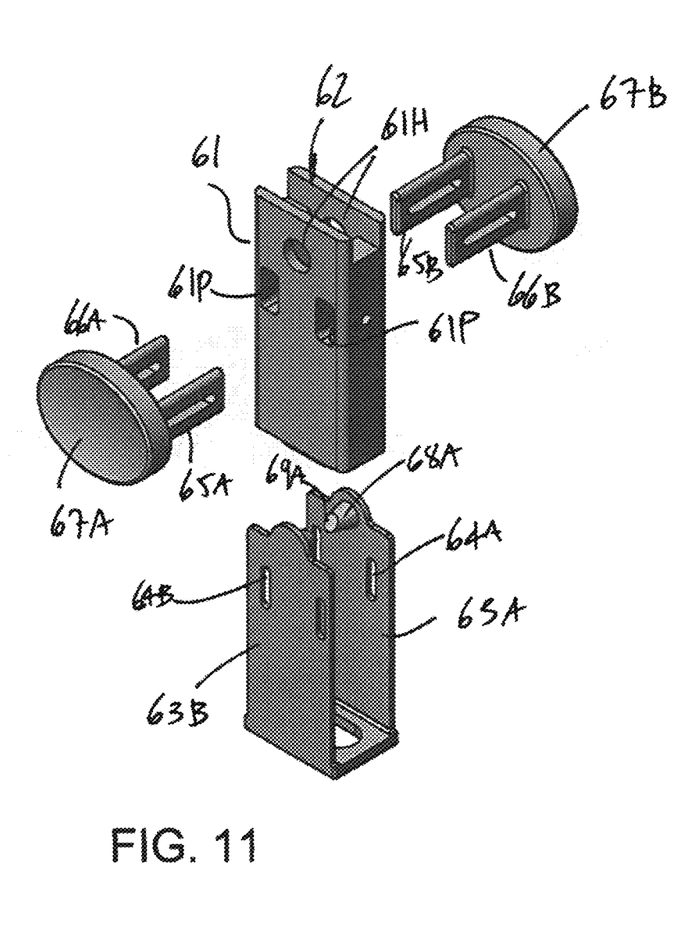
FIG. 11 is an exploded view of the quick connect system of FIG. 10.

The tongues 63 may be described as leaf springs, for example, as they are connected to a body of the receptacle 61 or are interconnected as part of the U-shaped bracket at one end, the connection end, and have a cantilevered end away from the connection end. In an embodiment, the tongues 63 are parallel with the walls of the receptacle 61, in a non-deformed state of the tongues 63. However, other arrangements are considered. The material and dimensions of the tongues 63 are selected such that the tongues 63 exhibit elastic deformation in quick connect use as described below.

The tongues 63 may have slots 64 in the cantilevered end. The slots 64 may extend through the tongues 63. An arm 65 is secured to the tongue 63 adjacent to one of the slots 64, and passes through the slot 64 in the opposite tongue 63, after passing through passage 61P in the receptacle 61. Another arm 66 may be secured to the tongue 63 adjacent to the other of the slots 64, though this is not necessary. Arms 66 may be shorter than arms 65, and be present to stabilize movement, and hence a smoother translation. The arms 65 and 66, if the same length, may help push uniformly on the leaf spring to avoid excessive one-sided twisting of the leaf spring. Arm 66 also passes through the slot 64 in the opposite tongue 63, after passing through passage 61P in the receptacle 61. Stated differently, the tongue 63A has an arm 65A, while arm 66A may or may not be connected to the tongue 63A. The arms 65A and 66A pass through the passages 61P, and through the slots 64B of the other tongue 63B, as they extend out of the receptacle 61. A detent 67A is located at the end of the arms 65A and 66A, and is located outside of the receptacle 61. The detent 67A may be referred to as a button, a push button, etc. If the arm 66A is not connected to the tongue 63A, it is connected to the other arm 65A by the detent 67A.

Figure 12:
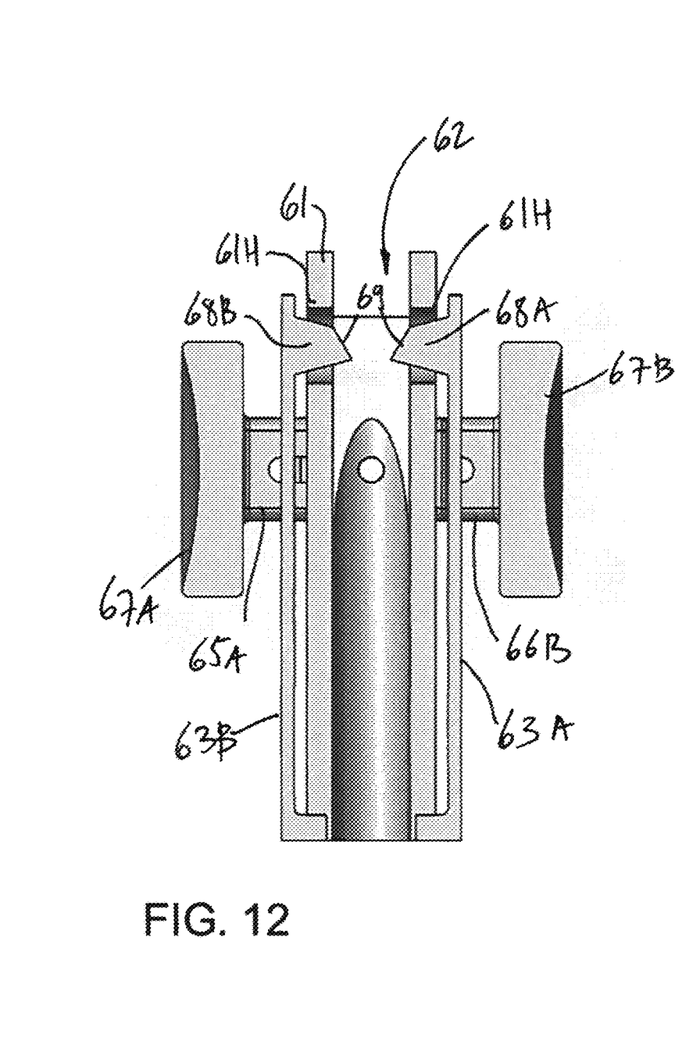
FIG. 12 is a longitudinal section view of the quick connect system of FIG. 10.
Figure 13:
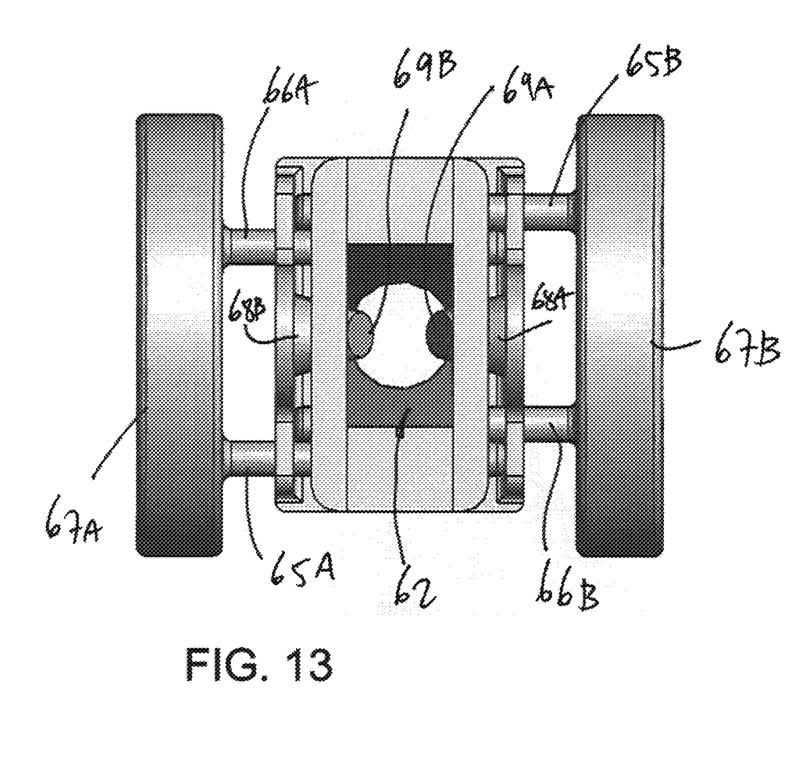
FIG. 13 is a top view of the quick connect system of FIG. 10.

The interplay between the tongues 63A and 63B is particularly well observed in FIGS. 12 and 13. The same arrangement may be replicated for the other tongue 63B, as it may have slots 64B, arms 65B and 66B, and detent 67B. The arms 65 and the arms 66 are in close proximity to one another. For example, a set of arms 65A and 65B share a common passage 61P and are parallel when the tongues 63A and 63B are in their relaxed state. Again, other arrangements are contemplated.

The arms 65 and 66 may be parallel to one another, and when applying a pinching force on the detents 67, as shown in FIG. 13, the cantilevered ends of the tongues 63 may be spaced apart from one another by elastic deformation, with the possibility of returning to the shape of FIGS. 12 and 13 by the resilience of the tongues 63.

Latch bolts 68 may be formed on the tongues 63, and may be located inside the inner cavity 62, via the holes 61H. The latch bolts 68 may for instance face one another, and may be in the cantilevered end. In an embodiment, the latch bolts 68 have a frustoconical shape, but other shapes are contemplated, including cylinders, spheres, etc. Moreover, an end surface 69 of the latch bolts 68 may be slanted, such that axes of the frustocones are not normal to the end surfaces 59.

Figure 10:
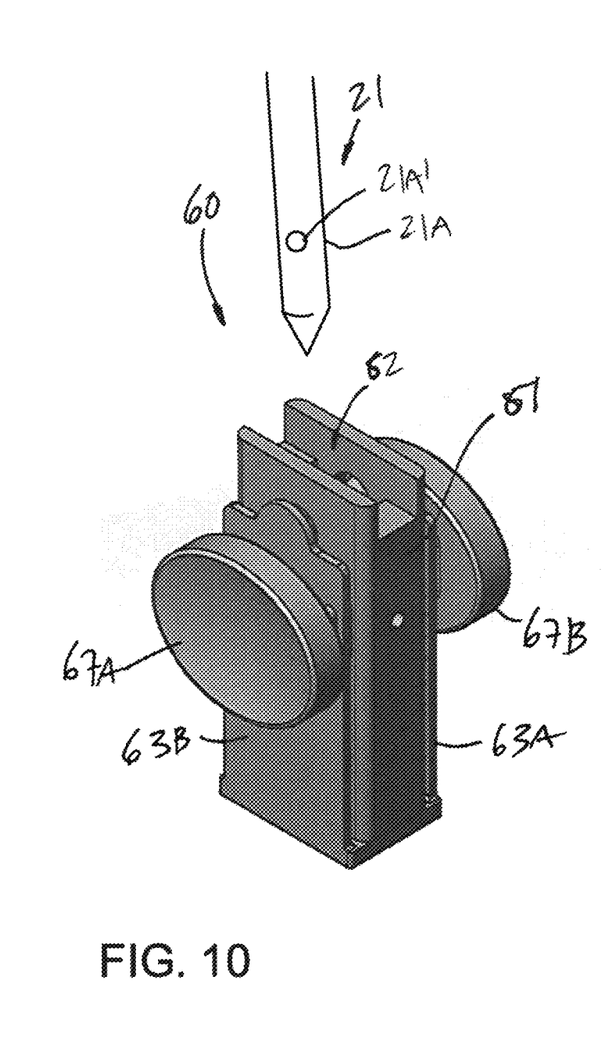
FIG. 10 is a perspective view of another embodiment of a quick connect system used in the surgical navigation tool assembly of FIG. 1.

Accordingly, with reference to FIGS. 10 to 13, a sequence of latching the tracker device 30 to the tool 20, using the quick connect system 60, is detailed. In FIG. 10, the working end 21A is moved in a proximal direction toward the receptacle 61 to be received in the inner cavity 62, along the longitudinal axis of the tool 20 for example. In an embodiment, the working end 21A has a thickness corresponding to a width of the inner cavity 62 to avoid lateral play. A bottom end of the working end 21A comes into contact with the latch bolts 68. Due to the frustoconical shape (or equivalent, such as hemispherical shape), the working end 21A slides along the latch bolts 68, and this may include sliding along the surfaces 69. This will result in a pivoting motion of the tongues 63. The latch bolts 68 then come into axial alignment with the sockets 21A' in the working end 21A. The biasing force resulting from the deformation of the tongues 63 (e.g., elastic deformation), will cause a penetration of the latch bolts 68 into the sockets 21A', i.e., a latch. The sockets 21A' are shaped for complementary engagement with the latch bolts 68, and this may include for example a complementary frustoconical hole shape. The sockets 21A' and the latch bolts 68 may be conically tapered joints that self-align for the tool 20 and the surface digitizer device 25 to be in a predetermined axial alignment.

The various components are sized such that when the working end 21A is at a given depth in the receptacle 61, the latch bolts 68 latch into the depressions sockets 21A'. Due to the shape of the bolts 68 and their mating engagement into the sockets 21A', the depth of penetration of the working end 21A in the receptacle 61 is known with precision. Hence, the tool 20 and the surface digitizer device 25 are locked to one another by the quick connect system 60. Using the geometry data of the tool 20 and of the surface digitizer device 25 (i.e., length, orientation), the position, and possibly the orientation, of the working end 21A may be calculated, using the position and orientation of the tracker device 30. The movements described above may occur automatically as a response to the manual insertion of the tool 20 in the surface digitizer device 25, or vice-versa. For this purpose, the quick connect system 60 is also referred to as "quick connect" as per terminology used for similar snap-it, manually induced automatic connections. Other expressions could be used to qualify the system 60, such as connection system, snap-fit system, etc.

To release the surface digitizer device 25 from the tool 20, a user may press on the detents 67 to displace the latch bolts 68 from their inserted engagement into the sockets 21A'. The tool 20 may be displaced in the distal direction, i.e., pulled away, to release the surface digitizer device 25 from the tool 20.

Figure 14:
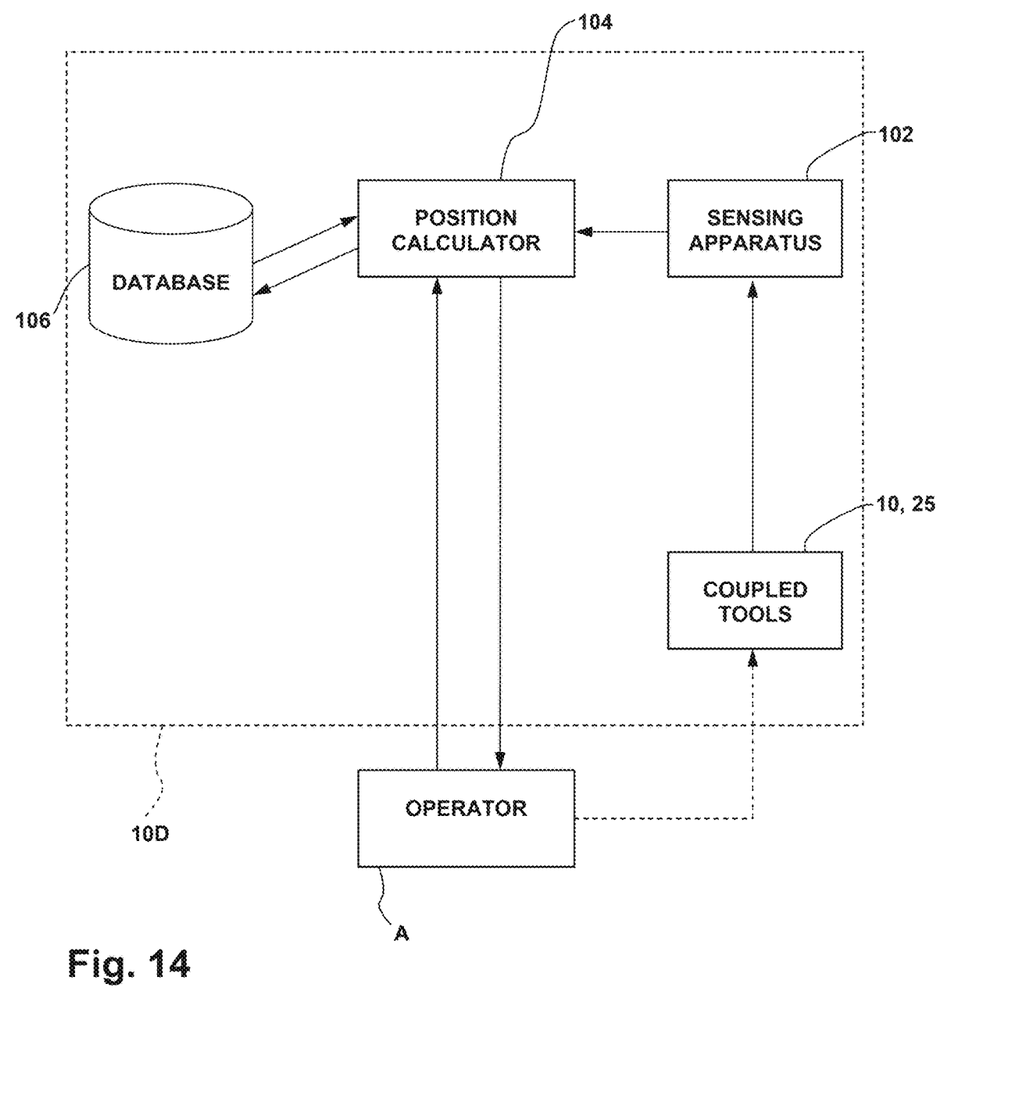
FIG. 14 is a block diagram of a computer-assisted surgery system using a surgical navigation tool assembly of the present disclosure.

Referring to FIG. 14, a computer-assisted surgery (CAS) system in accordance with the present disclosure is generally shown at 100. The CAS system 100 is for tracking the surgical navigation tool assembly 10. In the embodiment in which the surgical navigation tool assembly 10 is optical, the CAS system 100 has sensing apparatus 102, a position calculator 104 and a database 106. The position calculator 104 is connected to the sensing apparatus 102 and to the database 106. An operator A (e.g., a surgeon) is illustrated interacting with the position calculator 104 and handling the surgical navigation tool assembly 10.

The sensing apparatus 102 is provided for tracking the surgical navigation tool assembly 10. More precisely, the sensing apparatus 102 is compatible with the detectable devices 33 on the surgical navigation tool assembly 10. In an embodiment, the detectable devices are passive (such as the retro-reflective spheres 33). An optical tracking system, such as Polaris™ by Northern Digital Inc., is well suited for being used as the sensing apparatus 102. Other types of tracking systems can be involved, and not necessarily passive ones. Active tracking systems, including electromagnetic devices or sound emitters, are contemplated as being suitable for the present disclosure, as are inertial sensors.

Therefore, as illustrated in FIG. 14, the surgical navigation tool assembly 10 is tracked for position and orientation by the sensing apparatus 102. A position of the working end 21A of the surgical navigation tool assembly 10 may be as a function of the nature of the tool 20 that is part of the surgical navigation tool assembly 10, a position and/or orientation of the working end 21A being calculable as a function of the tracking for position and orientation of the tracker device 30 assembled to the tool 20 by the quick connect system 40, 50 or 60. Accordingly, the position and orientation tracking performed by the sensing apparatus 102 is forwarded in real time to the position calculator 104, which calculates a position of the working end 21A of the tool 20. The position calculator 104 must know the geometrical relation between the working end 21A of the tool 20 and the tracker device 30, which may be physically reproduced by the precision enabled by the use of the quick connect system 40, 50 or 60 described herein, of the tool 20 and the tracker device 30 are interconnected by one of the quick connect system 40, 50 or 60.

The position calculator 104 is typically part of a computer, PC station, having a CPU, RAM and operator interfaces, such as a display unit, keyboard, mouse, foot pedal, etc. The computer has a processing unit, featuring one or more processors; and a non-transitory computer-readable memory communicatively coupled to the processing unit and comprising computer-readable program instructions executable by the processing unit to perform functions such as those related to the position calculator 104. The database 106 is typically part of the PC station as the hard disk drive, and is used to store the points registered by the CAS system 100. The position calculator 104 performs the calculation of the position of the tip as a function of the position and orientation tracking by the sensing apparatus 102 and of the geometrical data that may be preprogrammed and is based on the type of tool 20, and the relation with the tracker device 30 as achieved via the quick connect system 40, 50 or 60. In an embodiment with one of the surface digitizer devices 25, the position calculator 104 performs the calculation of the position of the interface surface 25A of the surface digitizer device 25 as a function of the position and orientation tracking by the sensing apparatus 102 and of the geometrical data that may be preprogrammed for the tool 20 and for the surface digitizer device 25 and is based on the type of tool 20 and on the type of surface digitizer device 25 or other tool, and the coupling between the tool 20 and the surface digitizer device 25, as achieved via the quick connect system 40, 50 or 60

The nature of the tool 20 being used can be indicated by the operator A, for instance, using the operator interfaces. Once the nature of the surface digitizer device 25 is known by the position calculator 104, the position of the interface surface 25A of the registration tool 20 can be calculated.

The system 100 of FIG. 14 may therefore perform actions, steps, etc, including to: track a first component in space during computer-assisted surgery using a tracker device on the first component; to receive a notification that a second component is connected to the first component; to automatically calibrate an assembly of the first component and the second component using a planned positional alignment between the first component and the second component; and to track the second component assembled to the first component in space during computer-assisted surgery using the tracker device on the first component. Automatically calibrate may entail that no mechanical steps are required after coupling of the second component, such as touching surfaces in a calibration procedure. Automatically calibrate may allow a procedure to proceed with surgical steps (e.g., steps in which the second component contacts the body) as soon as the system 100 is informed of the coupling of the second component to the first component, with the calibration being virtual, e.g., the system retrieving a geometry of the assembly using the known planned positional coupling between the components. The system 100 may also be used to track the first component contacting human tissue during the computer-assisted surgery; to track the second component contacting human tissue during the computer-assisted surgery; to automatically calibrate the assembly without user input; to receive in the notification a confirmation of an identity of the second component; to visually recognize the second component when automatically calibrating; to receive the notification from a user; to prompt a user to confirm the connection of the second component to the first component, prior to receiving the notification.

EXAMPLES

Example 1 can include or use subject matter such as a surgical tool assembly comprising: a first component; a second component; a tracker device connected at least to the first component; and a quick connect system for releasably connecting the first component to the second component, the quick connect system including a male and female engagement, a latch mechanism for latching the first component to the second component, and complementary features on the first component and on the second component to ensure a planned positional alignment between the first component and the second component upon latching of the male and female engagement, for tracking of the second component with the tracker device.

Example 2 can include, or can optionally be combined with the subject matter of Example 1, to optionally include the second component that defines a receptacle for receiving a portion of the first component in the male and female engagement.

Example 3 can include, or can optionally be combined with the subject matter of Example 1 or 2, to optionally include the complementary features including at least one socket on one of the components, and at least one penetrating component on the other of the components.

Example 4 can include, or can optionally be combined with the subject matter of Example 3, to optionally include the at least one socket that is on the first component.

Example 5 can include, or can optionally be combined with the subject matter of Example 3 or 4, to optionally include the at least one penetrating component that has a spherical portion, and the socket that has a truncated sphere geometry.

Example 6 can include, or can optionally be combined with the subject matter of Example 3 or 4, to optionally include the at least one penetrating component that has a frusto-conical portion, and the socket that has a complementary geometry.

Example 7 can include, or can optionally be combined with the subject matter of Example 6, to optionally include the frusto-conical portion that has a slanted end surface.

Example 8 can include, or can optionally be combined with the subject matter of Examples 1 to 7, to optionally include the latch mechanism that opposes a biasing force against a penetration in the male and female engagement of the first component and the second component, the biasing force being axially against a direction of the penetration.

Example 9 can include, or can optionally be combined with the subject matter of Examples 1 to 7, to optionally include the latch mechanism that opposes a biasing force against a penetration in the male and female engagement of the first component and the second component, the biasing force being transverse to a direction of the penetration.

Example 10 can include, or can optionally be combined with the subject matter of Example 9, to optionally include a pair of detents on opposite sides of the male and female engagement to pinch release the latching of the male and female engagement.

Example 11 can include, or can optionally be combined with the subject matter of Examples 1 to 10, to optionally include the first component that is a registration pointer.

Example 12 can include, or can optionally be combined with the subject matter of Example 11, to optionally include the second component that is a surface digitizer device.

Example 13 can include, or can optionally be combined with the subject matter of Examples 11 or 12, to optionally include the tracker device that is an optical tracker device.

Example 14 can include, or can optionally be combined with the subject matter of Examples 1 to 10, to optionally include the first component that is a robotic arm.

Example 15 can include, or can optionally be combined with the subject matter of Example 14, to optionally include the second component that is a tool manipulated by the robotic arm.

Example 16 can include, or can optionally be combined with the subject matter of Examples 14 or 15, to optionally include the tracker device that is an optical tracker device.

Example 17 can include or use subject matter such as a system for tracking a surgical tool assembly in computer-assisted surgery, comprising: a processing unit, featuring one or more processors; and a non-transitory computer-readable memory communicatively coupled to the processing unit and comprising computer-readable program instructions executable by the processing unit to: track a first component in space during computer-assisted surgery using a tracker device on the first component; receive a notification that a second component is connected to the first component; automatically calibrate an assembly of the first component and the second component using a planned positional alignment between the first component and the second component; and track the second component assembled to the first component in space during computer-assisted surgery using the tracker device on the first component.

Example 18 can include, or can optionally be combined with the subject matter of Example 17, to optionally include the computer-readable program instructions that are further executable to track the first component contacting human tissue during the computer-assisted surgery.

Example 19 can include, or can optionally be combined with the subject matter of Examples 17 or 18, to optionally include the computer-readable program instructions that are further executable to track the second component contacting human tissue during the computer-assisted surgery.

Example 20 can include, or can optionally be combined with the subject matter of Examples 17 to 19, to optionally include the computer-readable program instructions that are further executable to automatically calibrate the assembly without user input.

Example 21 can include, or can optionally be combined with the subject matter of Examples 17 to 20, to optionally include the computer-readable program instructions that are further executable to receive in the notification a confirmation of an identity of the second component.

Example 22 can include, or can optionally be combined with the subject matter of Example 17 to 21, to optionally include the computer-readable program instructions that are further executable to visually recognize the second component when automatically calibrating.

Example 23 can include, or can optionally be combined with the subject matter of Examples 17 to 22, to optionally include the computer-readable program instructions that are further executable to receive the notification from a user.

Example 24 can include, or can optionally be combined with the subject matter of Example 23, to optionally include the computer-readable program instructions that are further executable to prompt a user to confirm the connection of the second component to the first component, prior to receiving the notification.

Example 25 can include, or can optionally be combined with the subject matter of Examples 17 to 22, to optionally include the first component and the second component.

Example 26 can include, or can optionally be combined with the subject matter of Example 25, to optionally include the first component that is a registration pointer.

Example 27 can include, or can optionally be combined with the subject matter of Example 26, to optionally the second component that is a surface digitizer device.

Example 28 can include, or can optionally be combined with the subject matter of Examples 26 to 28, to optionally include the tracker device that is an optical tracker device.

Example 29 can include, or can optionally be combined with the subject matter of Example 25, to optionally include the first component that is a robotic arm.

Example 30 can include, or can optionally be combined with the subject matter of Example 29, to optionally include the second component that is a tool manipulated by the robotic arm.

Example 31 can include, or can optionally be combined with the subject matter of Examples 29 to 30, to optionally include the tracker device is an optical tracker device.

Each of these non-limiting examples can stand on its own, or can be combined in various permutations or combinations with one or more of the other examples.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A surgical tool assembly comprising:
    a first component having a first working end for performing actions in contact with human tissue, the first working end being tracked when in contact with human tissue in a first use;
    a second component having a second working end for performing actions in contact with human tissue, the second working end being tracked when in contact with human tissue in a second use;
    a tracker device connected at least to the first component; and
    a quick connect system for releasably connecting the first component to the second component, the quick connect system including a male and female engagement, a latch mechanism including at least one latch for latching the first component to the second component, and complementary features on the first component and on the second component to ensure a planned positional alignment between the first component and the second component upon latching of the male and female engagement, for tracking of the second component with the tracker device;
    wherein the complementary features on the first component and on the second component penetrate one into another at a depth of penetration of the male engagement into the female engagement corresponding to the planned positional alignment;
    wherein the surgical tool assembly converts from the first use to the second use when the first component to the second component are releasably connected; and
    wherein the at least one latch opposes a biasing force against a penetration in the male and female engagement of the first component and the second component.

2. The surgical tool assembly according to claim 1, wherein the second component defines a receptacle for receiving a portion of the first component in the male and female engagement.

3. The surgical tool assembly according to claim 1, wherein the complementary features including at least one socket on one of the components, and at least one penetrating component on the other of the components.

4. The surgical tool assembly according to claim 3, wherein the at least one socket is on the first component.

5. The surgical tool assembly according to claim 3, wherein the at least one penetrating component has a spherical portion, and the socket has a truncated sphere geometry.

6. The surgical tool assembly according to claim 3, wherein the at least one penetrating component has a frusto-conical portion, and the socket has a complementary geometry.

7. The surgical tool assembly according to claim 6, wherein the frusto-conical portion has a slanted end surface.

8. The surgical tool assembly according to claim 1, wherein the biasing force is axially against a direction of the penetration.

9. The surgical tool assembly according to claim 1, wherein the biasing force is transverse to a direction of the penetration.

10. The surgical tool assembly according to claim 9, including a pair of detents on opposite sides of the male and female engagement to pinch release the latching of the male and female engagement.

11. The surgical tool assembly according to claim 1, wherein the first component is a registration pointer.

12. The surgical tool assembly according to claim 11, wherein the second component is a surface digitizer device.

13. The surgical tool assembly according to claim 11, wherein the tracker device is an optical tracker device.

14. The surgical tool assembly according to claim 1, wherein the first component is a robotic arm.

15. The surgical tool assembly according to claim 14, wherein the second component is a tool manipulated by the robotic arm.

16. The surgical tool assembly according to claim 14, wherein the tracker device is an optical tracker device.

17. The surgical tool assembly according to claim 1, wherein the latch mechanism includes a pair of the at least one latch.

18. A computer-assisted surgery system for comprising:
the surgical tool assembly according to claim 1;
a sensing apparatus for tracking the tracker device of the surgical tool assembly;
a processing unit, featuring one or more processors, and
a non-transitory computer-readable memory communicatively coupled to the processing unit and comprising computer-readable program instructions executable by the processing unit to:
track the first component in space during computer-assisted surgery using the tracker device on the first component,
receive a notification that the second component is connected to the first component, automatically calibrate an assembly of the first component and the second component using the planned positional alignment between the first component and the second component, and track the second component assembled to the first component in space during computer-assisted surgery using the tracker device on the first component.

\* \* \* \* \*